(12) United States Patent
Buchert et al.

(10) Patent No.: US 6,959,034 B2
(45) Date of Patent: *Oct. 25, 2005

(54) CDMA SYSTEM TRANSMISSION MATRIX COEFFICIENT CALCULATION

(75) Inventors: Ryan Samuel Buchert, Phoenixville, PA (US); Chayil S. Timmerman, Harleysville, PA (US); Peter Edward Becker, Coatesville, PA (US); Muhammad Usman Fazili, Jeffersonville, PA (US)

(73) Assignee: InterDigital Technology Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/920,137

(22) Filed: Aug. 17, 2004

(65) Prior Publication Data

US 2005/0013346 A1 Jan. 20, 2005

Related U.S. Application Data

(63) Continuation of application No. 10/040,994, filed on Dec. 28, 2001, now Pat. No. 6,792,032.

(51) Int. Cl.$^7$ .............................................. H04K 1/00
(52) U.S. Cl. ..................... 375/147; 375/130; 370/335; 370/342

(58) Field of Search ................................. 375/130, 147, 375/146; 370/335, 342; 708/315, 514

(56) References Cited

U.S. PATENT DOCUMENTS

| | | | |
|---|---|---|---|
| 5,235,537 A | | 8/1993 | McWhirter et al. |
| 6,173,009 B1 | | 1/2001 | Gu |
| 6,792,032 B2 | * | 9/2004 | Buchert et al. ............. 375/147 |
| 2004/0001465 A1 | * | 1/2004 | Timmerman et al. ....... 370/335 |

* cited by examiner

Primary Examiner—Temesghen Ghebretinsae
(74) Attorney, Agent, or Firm—Volpe and Koenig, P.C.

(57) ABSTRACT

An apparatus and method for data processing particularly useful in combining convolutions of the spreading code, scrambling code and channel response in order to construct a system transmission coefficient matrix, while maintaining the same circuit size and execution time relative to performing each convolution separately. One register for processing real channel response values and a second register for processing imaginary channel response values, are used for moving channel responses through the convolution. In place of multipliers, an optimized minimum number of adders connected in a pyramid configuration are used to perform the necessary multiplication of the codes, for simplicity of construction. By including the channel code transformation from binary representation to complex representation as part of the overall method, unnecessary adders are eliminated from the apparatus.

7 Claims, 5 Drawing Sheets

|  |  |  |
|---|---|---|
| W-15 ENABLED VALUES | | 000000000000000 |
| 0 | W-15 ENABLED VALUES | 00000000000000 |
| 00 | W-15 ENABLED VALUES | 0000000000000 |
| 000 | W-15 ENABLED VALUES | 000000000000 |
| 0000 | W-15 ENABLED VALUES | 00000000000 |
| 00000 | W-15 ENABLED VALUES | 0000000000 |
| 000000 | W-15 ENABLED VALUES | 000000000 |
| 0000000 | W-15 ENABLED VALUES | 00000000 |
| 00000000 | W-15 ENABLED VALUES | 0000000 |
| 000000000 | W-15 ENABLED VALUES | 000000 |
| 0000000000 | W-15 ENABLED VALUES | 00000 |
| 00000000000 | W-15 ENABLED VALUES | 0000 |
| 000000000000 | W-15 ENABLED VALUES | 000 |
| 0000000000000 | W-15 ENABLED VALUES | 00 |
| 00000000000000 | W-15 ENABLED VALUES | 0 |
| 000000000000000 | W-15 ENABLED VALUES | |

$A^H$ MATRIX FOR SF = 1

*FIG. 6*

CDMA SYSTEM TRANSMISSION MATRIX COEFFICIENT CALCULATION

CROSS REFERENCE TO RELATED APPLICATION(S)

This application is a continuation of U.S. patent application Ser. No. 10/040,994, filed Dec. 28, 2001, now U.S. Pat. No. 6,792,032 which is incorporated by reference as if fully set forth.

BACKGROUND

The present invention relates to wireless digital communication systems. More particularly, the present invention relates to a method and apparatus for convolution of spreading code, scrambling code and channel response within a wireless TD-CDMA communication receiver to calculate system transmission matrix coefficients.

During communications in a TD-CDMA system such as specified by the Third Generation Partnership Project (3GPP), each signal burst between a base station and a user equipment (UE) is transmitted and received along a frame structure that is broken into time slots. FIG. 1 shows the structure of a communication burst time slot comprising a predetermined midamble, specifically assigned by a base station to a UE for channel estimation purposes, located between two data symbol bursts. The midamble information is characterized by a number of chips, where $T_C$ represents the chip period and $L_m$ is the midamble length. The midamble chips are transformed by a filter process in the receiver into a channel response consisting of real and imaginary components. Because a TD-CDMA system allows several UEs to be assigned to the same time slot, each has a unique spreading code and spreading factor tagged to it to distinguish one UE's midamble channel representation from another. Scrambling codes are attached to a signal to distinguish one base station from another, thereby preventing inter-base station interference, which potentially occurs when a UE is in the range of two nearby base stations.

As a wireless transmission travels through the air between a transmitter and a receiver, signal reflections and external noise effects create a received signal that is different from its original state. Therefore, within the communication system, it is useful to develop a representation of the known system transmission characteristics unique to the particular base station and UE. In 3GPP systems, a system transmission matrix A of coefficient values, and/or its complex conjugate transpose $A^H$, is used for this purpose. Applying the received signal to the system transmission matrix coefficients is a way to extract the original signal data from the externally altered signal that was received.

SUMMARY

The present invention provides an apparatus and method for data processing particularly useful in combining convolutions of the spreading code, scrambling code and channel response in order to construct a system transmission coefficient matrix, while maintaining the same circuit size and execution time relative to performing any one convolution separately.

The invention includes an apparatus and method for inter alia processing a series of dual element data values $V_1$ to $V_x$ such as complex number representations where data value $V_m$, for each integer m from 1 to x, corresponds to a first element $A_m$ and a second element $B_m$, with a N bit binary value, where N is a positive even integer, to produce a series of data values $V'_1$ to $V'_y$ where data value $V'_p$, for each integer p from 1 to y, corresponds to a first element $A'_p$ and a second element $B'_p$. Preferably, the series of data values $V_1$ to $V_x$ represent channel response values of a communication signal that has a spreading factor of $2^M$ where M is an integer and $2^M \leq N$. In such case, the N bit binary value represents a channel code value associated with the communication signal and the series of data values $V'_1$ to $V'_y$ represents a row of values of a system transmission matrix. N is preferably a power of 2.

A first element shift register $R_1$ and a second element shift register $R_2$ are provided. Each register $R_1, R_2$ has a series of N locations Ci for each integer i from 1 to N. Each register $R_1, R_2$ is associated with a first component adder circuit $A_{1,1}$, $A_{1,2}$, respectively, and a second component adder circuit $A_{2,1}, A_{2,2}$, respectively.

Each adder circuit has a series of N/2 selectively controllable inputs $I_k$, for each integer k from 1 to N/2. Each adder circuit input is coupled with a different register location to receive data therefrom. Each adder circuit input is controllable via a control bit associated with its respective register location, where the control bits collectively correspond to the N bit binary value. Each control bit $B_i$ associated with a location Ci of register $R_R$ is the same as the control bit $B_i$ associated with corresponding location Ci of register $R_I$ for each integer i from 1 to N, such that the input receives data from the location to which it coupled as a value or an inverse value of the received data, dependent upon the value of the control bit. Each adder circuit has an output for outputting the sum of the values received by its respective controllable inputs.

Preferably, the first component adder circuit $A_{1,1}$ is coupled with the register $R_1$ such that input $I_k$ receives data from register location C2k-1, for each integer k from 1 to N/2. The second component adder circuit $A_{1,2}$ is coupled with the register $R_1$ such that input $I_k$ receives data from register location C2k, for each integer k from 1 to N/2. The first component adder circuit $A_{1,2}$ is coupled with the register $R_2$ such that input $I_k$ receives data from register location C2k, for each integer k from 1 to N/2. The second component adder circuit $A_{2,2}$ is coupled with the register $R_2$ such that input $I_k$ receives data from register location C2k-1, for each integer k from 1 to N/2.

A first component combiner circuit is coupled to the outputs of the first component adder circuits $A_{1,1}, A_{1,2}$ for outputting a first element value $A'_p$ of a processed value $V'_p$. A second component combiner circuit is coupled to the outputs of the second component adder circuits $A_{2,1}, A_{2,2}$ for outputting a second element value $B'_p$ of a processed value $V'_p$.

The registers $R_R, R_I$ are operable to shift the data of their respective locations and receive new data to thereafter generate a next processed value $V'_{p+1}$. Preferably, the registers $R_1, R_2$ are operable to shift the data of respective locations Ci-1 to locations Ci for each integer i from 2 to N and receive new data in location C1 to thereafter generate the next processed value.

Preferably, a control circuit is provided that operatively controls the registers and adder circuits based on the spreading factor of a communication corresponding to the data value series to be processed. The control circuit is operative to sequentially input the series of data values $V_1$ to $V_x$ followed by a series of N-1 zero values to the registers N/2M times to produce N/2M series of data values $V'_1$ to $V'_y$, where y=x+N-1, each representing a row of values of the system transmission matrix. The control circuit is operative to selectively enable and disable the inputs of the adder circuits when $2^M<N$ such that each time the series of data values $V_1$ to $V_x$ is input to the registers, a different set of $2^M$ inputs are enabled from each register with all other adder inputs being disabled.

Preferably, registers $R_1$ and $R_2$ are 16-location type (N=16) with F bits per location, are used for moving channel responses through the convolution. In place of multipliers, an optimized minimum number of adders connected in a pyramid configuration are used to perform the necessary multiplication of the codes, for simplicity of construction. By including the channel code transformation from binary representation to complex representation as part of the overall method, unnecessary adders are eliminated from the apparatus.

Other objects and advantages will be apparent to those skilled in the art from the following descriptions.

BRIEF DESCRIPTION OF THE DRAWINGS

FIG. 6 shows dimensions of a system transmission matrix complex conjugate transpose $A^H$ for spreading factor of 1.

DESCRIPTION OF THE PREFERRED EMBODIMENTS

Figure 1:
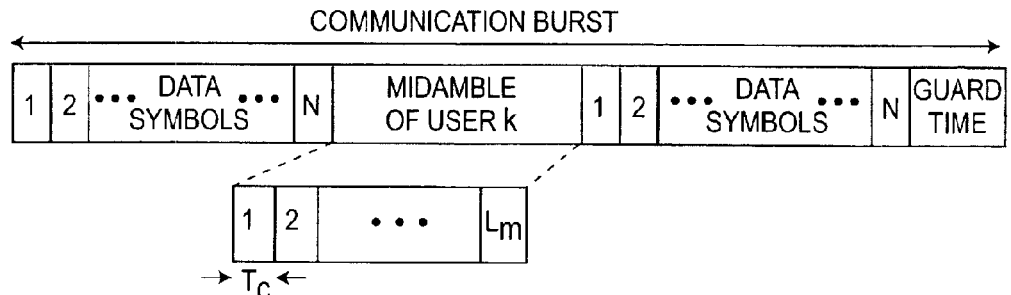
FIG. 1 shows a time slot structure comprising a midamble of multiple chips, on which the present invention operates.

Presently preferred embodiments are described below with reference to the drawing figures wherein like numerals represent like elements throughout.

Figure 2A:
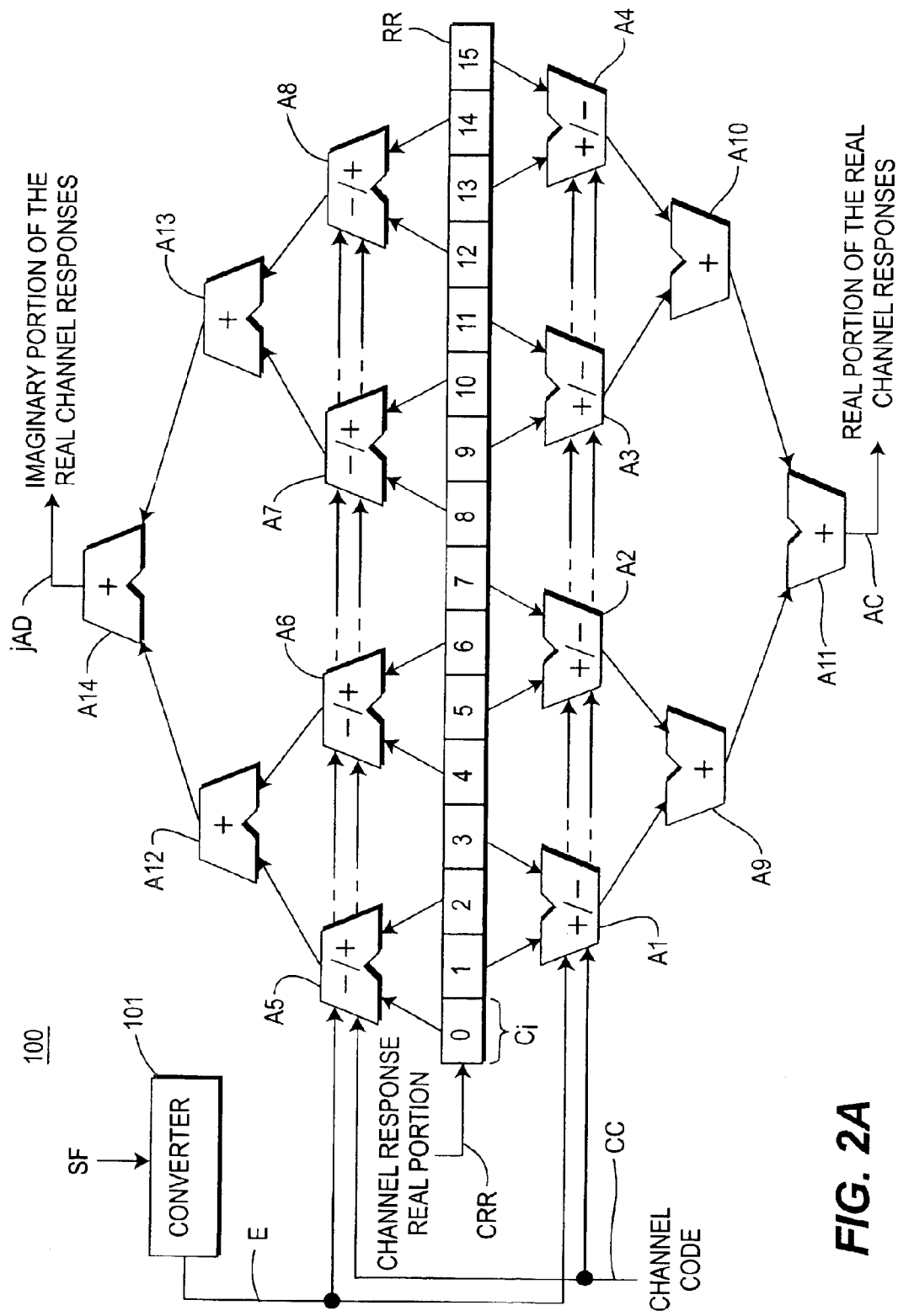
FIG. 2A shows the apparatus for convolving the real portion of the channel response.
Figure 2B:
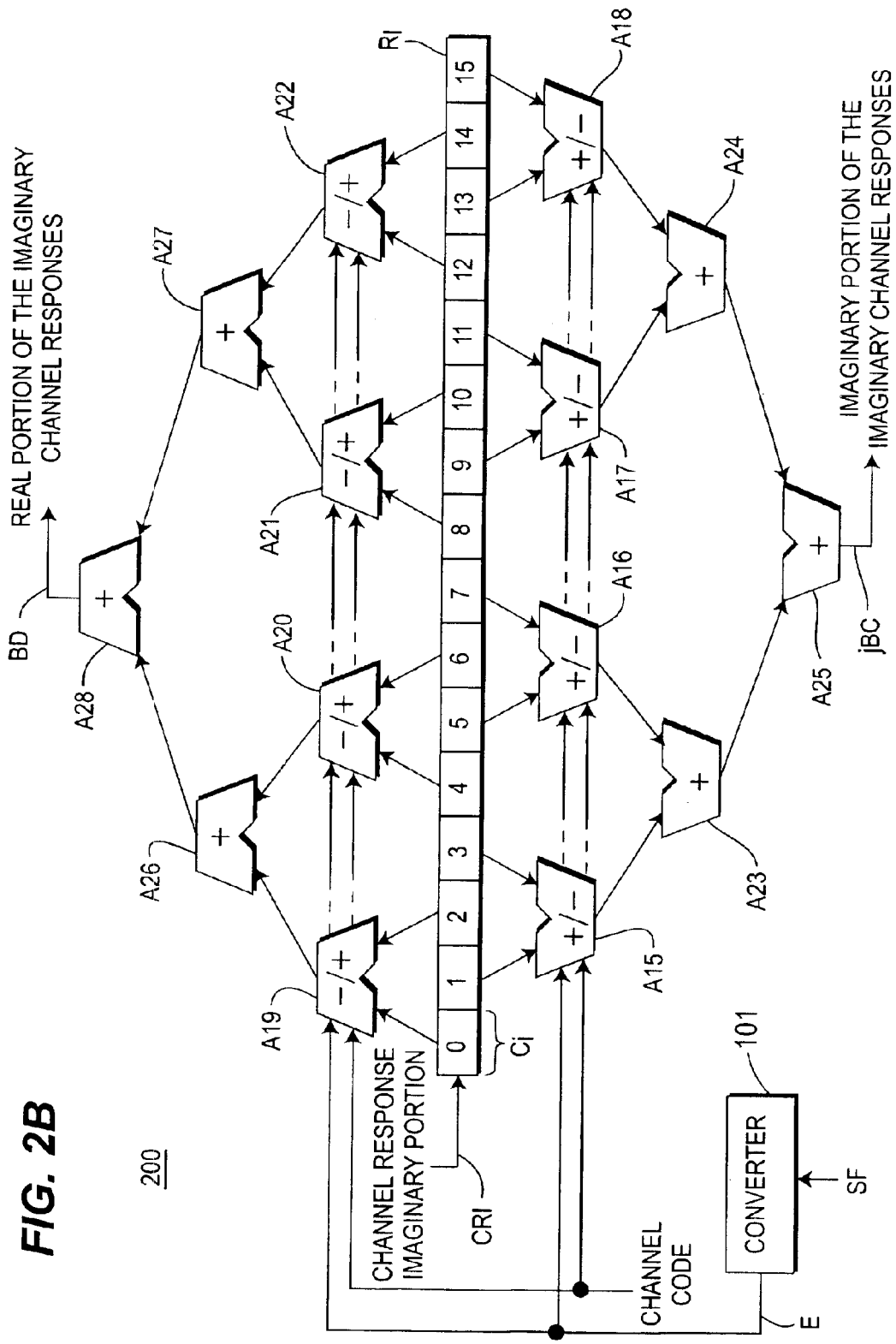
FIG. 2B shows the apparatus for convolving the imaginary portion of the channel response.

Referring to FIGS. 2A and 2B, the circuit diagrams 100 and 200, respectively, which perform convolution of a series of real and imaginary channel response chip values associated with a TD-CDMA time slot, are illustrated. The channel response values are divided into a real portion CRR and an imaginary portion CRI. The real channel response CRR is processed by the circuit 100 while the imaginary channel response CRI is processed in tandem by the circuit 200.

Figure 4:
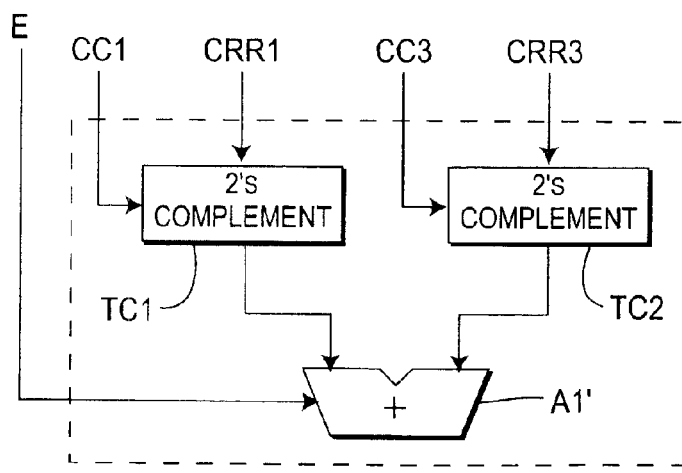
FIG. 4 shows a preferred circuit for adder tree inputs of FIG. 2A and FIG. 2B.

In FIG. 2A, register $R_R$ is preferably a 16-location register, which receives the real portion of the channel response CRR. Each location Ci (i=0 to 15) of register $R_R$ has F bits per location where F is a selected data bit size, preferably 10. The number of locations corresponds with the preferred channel code size, which is currently specified as 16 in 3GPP and is preferably a power of 2 in number. The real component circuit 100 includes a plurality of components A1–A14, each adder component has an adder having two inputs and a single output which is the sum of the two inputs. Adder components A1–A8 are preferably configured as illustrated in FIG. 4. Adder components A9–A14 are preferably simple adders.

Adder components A1, A2, A3, A4 receive input from the odd locations of register $R_R$ and perform either addition or subtraction on their pair of inputs. Similarly, adder components A5, A6, A7 and A8 are coupled to register $R_R$ to perform addition or subtraction on the channel response values, but only operate on the even locations of register $R_R$. Collectively, adder components A1–A4, A9–A11 form one adder tree circuit having inputs defined by components A1–A4 and an output defined by component A11. Similarly, adder components A5–A8, A12–A14 form a second adder tree circuit. The association of the adder tree circuits with the register $R_R$ is such that real and imaginary portions of processing values of the CRR values being processed through register $R_R$ are computed.

Acting as a control signal, a channel code CC having bits CC0 through CC15 are input to the adder components A1 through A8. The binary channel codes control whether adder components A1 through A8 perform an addition or a subtraction dependent upon the respective control bit, preferably addition when the channel code CC bit=0 and subtraction when the channel code CC bit=1.

FIG. 4 illustrates a preferred construction of input adder component A1 having an adder A1' and two two's complement devices TC1, TC2. Inputs CRR1 and CRR3 receive the real channel response values contained in second and fourth locations C1, C3 of register $R_R$, which are processed by two's complement devices TC1, TC2. CCR value addition or subtraction is accomplished by the adder A1' summing the output of the two's complement devices TC1, TC2. The two's complement devices TC1, TC2 operate on the input values by either passing the value or its two's complement through to the adder A1'. The second bit CC1 of the 16 bit channel code control signal CC determines the operation performed by the two's complement device TC1 while the fourth bit CC3 of the channel code determines the operation performed by the two's complement device TC2.

Referring to FIG. 2A, adder A9 performs a summation of the sums performed by A1 and A2. Likewise, adder A10 sums the sum of A3 with the sum of A4, adder A12 performs the sum of A5 and A6, and adder A13 sums A7 with A8. Adder A11 produces output AC, the real portion of the real channel response values, by adding the sum of A9 with the sum of A10. Output jAD, the imaginary portion of the real channel response values, is the sum produced by adder A14, which is the sum of the outputs of adders A12 and A13.

Processing circuit 200, shown in FIG. 2B, is constructed similarly to the circuit 100 shown in FIG. 2A. However, the shift register $R_I$ receives the imaginary portion of the channel response CRI. Adder components A15 through A28 correspond with adder components A1 through A14 to provide the register $R_I$ with two associated adder tree circuits. The two outputs of the adder tree circuits of circuit 200 shown in FIG. 2B are opposite of those shown in FIG. 2A for circuit 100, in that a value corresponding to a real portion shown as output BD comes from the even locations of register $R_I$ and a value corresponding to an imaginary output jBC is the final sum of the odd numbered locations of register $R_I$. The configurations of real and imaginary outputs relative to even and odd register locations could be completely reversed, and identical results could be obtained. Specifically, with registers $R_R$ and $R_I$ swapped in FIGS. 2A and 2B, output AC and jBC would be derived from even register locations and outputs BD and jAD would be derived from odd register locations.

Although the registers of FIGS. 2A and 2B have been represented with 16 locations apiece, convolution of channel response values in accordance with the present invention could generally be achieved using registers having $2^N$ register locations and a combination of more or less adders all configured accordingly to perform the sums on the even and odd register locations.

The four output values AC, BD, jAD and jBC of the circuits 100 and 200 represent real and imaginary portions of a multiplication operation as shown in Equation 1:

$$A^H = (A+jB)*(C+jD) \quad \text{Equation 1}$$

where A is the real portion of the channel response, B is the imaginary portion of the channel response and where C corresponds to bits C1, C3, C5, C7, C9, C11, C13, C15 of the channel code CC, D corresponds to bits C0, C2, C4, C6, C8, C10, C12, C14 of the channel code. Each channel code bit represents a value that is either purely real or purely imaginary. Accordingly, the adder tree circuits can be hard-wired to either all of the odd or all of the even locations of the registers $R_R$ and $R_I$. The adder trees used in accordance with the present invention for determining which channel code bits are real or imaginary eliminates the need for multipliers, which would consume hardware space to a greater degree.

Figure 3:
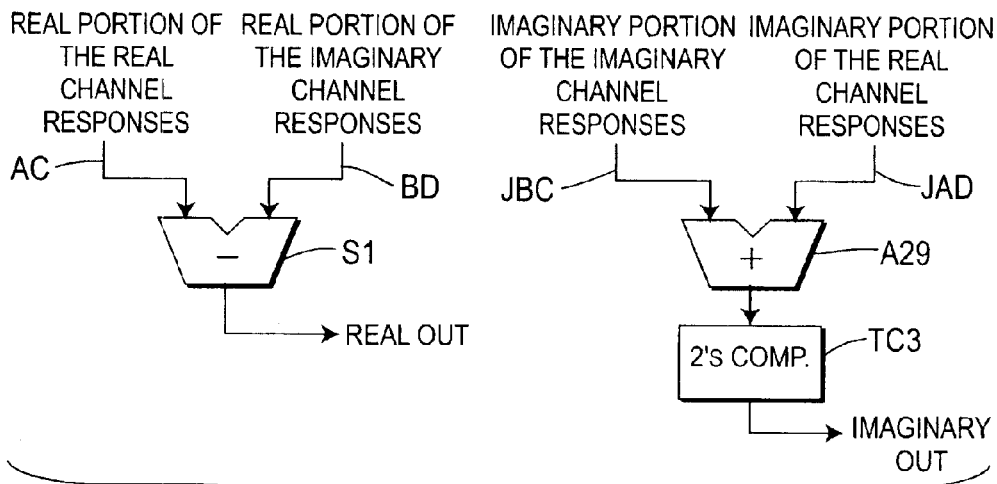
FIG. 3 shows the apparatus for summing the outputs of the FIG. 2A and FIG. 2B apparatuses to produce real and imaginary output used to construct the system transmission coefficient matrix.

As shown in FIG. 3, additional circuitry is provided to combine the outputs of the adder trees of circuits 100, 200 to produce coefficient values corresponding to real and imaginary output values used for constructing the system transmission coefficient matrix complex conjugate transpose $A^H$. A subtracter S1 is associated with output AC of circuit 100 and output BD of circuit 200 to subtract the real portion of the processed real channel response signal and the real portion of the imaginary channel response signal. An adder A29 is associated with output jBC of circuit 200 and jAD of circuit 100 to sum the imaginary portion of the processed imaginary channel response signal and the imaginary portion of the real channel response signal. The sum produced by adder A29 is then passed through two's complement device TC3 for the imaginary output, which produces the complex conjugate of the A matrix. In an alternate embodiment of the present invention, the device TC3 is omitted thereby allowing the circuits of FIGS. 2A, 2B and 3 to produce the A matrix, which may also be useful in the processing of CDMA signals.

Preferably, the channel code CC is a 16 bit long binary number created by an EXCLUSIVE OR (XOR) operation of a 16 bit long scrambling code S and a modified 16 bit spreading code SCM as shown by Equation 2.

$$CC = S \text{ XOR } SCM \quad \text{Equation 2}$$

To produce a 16 bit SCM, a spreading code SC is modified by repeating the first SF digits of the spreading code SC until a 16 bit value is produced, where SF is a spreading factor value. For example, with the spreading factor SF 8, and the spreading code SC=0011 1111 0000 1010, the modified spreading code SCM=0011 1111 0011 1111, i.e. the first eight bits of SC being repeated twice. Constructing a channel code in this way provides the means necessary for convolution of the channel response CR values, the spreading code SC and the scrambling code S. The channel code CC remains fixed for the duration of the convolution process, since the spreading factor SF and the scrambling code S is set for a particular UE/base station communication signal being processed. By combining all of the operations (i.e., the combination of the scrambling code and spreading code) at once instead of performing them in individual processing stages, multipliers are eliminated. The number of adders required is also optimized with the disclosed design.

The 16 bit channel code CC is continuously present as a control signal to the first level adder components A1 through A8 of FIG. 2A and adder components A15 through A22 of FIG. 2B for determining whether the values input to an adder are to be negated or are to remain the same prior to summing. As noted above, each adder is controlled by a channel code bit correlating with the registered locations that are inputs to that adder. For example, adder A1 is controlled by channel code bits CC1 and CC3, which corresponds with register $R_R$ locations C1 and C3 as shown in FIG. 2A.

Additionally, the operation of circuits 100, 200 and the adder tree circuits are controlled by the spreading factor SF. In the preferred embodiment where 16 location registers are used, the possible values for the spreading factor are 1, 2, 4, 8 or 16. The number of complete processing cycles for each set of channel responses CR to be performed by each of the circuits 100, 200 is based on the relationship 16/SF. For example, for spreading factor SF=16, the processing circuits 100, 200 operate for one cycle to process the set of CR values; for SF=4 the CR values are processed 4 times (16/4).

The registers initially have zero values at all locations. Once the cycle process begins, the first CR value is initially input to location C0 and the contents of each location Ci (value=0) is shifted to the right by one location. Location C0 of register $R_R$ receives the real component and location C0 of register $R_I$ receives the imaginary component. A complex coefficient value is calculated and output from the combining circuit of FIG. 3 based on the register values and selectively controlled adder trees as described above. The values of the register locations are then shifted again so that register location Ci for i>1 receives the value from register location Ci-1 and the next CR value is input to location C0, for each register $R_R$, $R_I$, respectively. The process then repeats for the duration of the cycle as the entire set of CR values are sequentially input into locations C0–C15. When all CR values of the set have been input, processing continues while a zero value is input to location C0 and each subsequent location until the last CR value is shifted out of location C15. Accordingly, for a CR set of N values, there are N+15 output values during each operational cycle. Generally, where the system is configured with X register locations, the operation cycle produces N+(X−1) output values from a set of N values.

The number of active inputs to the adder tree circuits in each process cycle is equal to 16/SF. A different set of inputs is active for each cycle when the CR values are processed more than once, i.e. SF≠16. For spreading factor SF=8, the first operation cycle is controlled by the first eight bits of the channel code CC0 through CC7. Thus, the inputs of adder components A1, A2, A5, A6 of FIG. 2A and adder components A15, A16, A19 and A20 of FIG. 2B are active to receive values from locations C0 through C7. During this first operation, all remaining inputs operate as if receiving a value of zero.

During a second cycle, the inputs for adder components A3, A4, A7, A8 and A17, A18, A21, A22 are active to receive data from the registers $R_R$ and $R_I$ and the other adder tree inputs are deactivated. For a spreading factor SF=2, the active inputs are preferably from register locations C0, C1 for the first cycle, C2, C3 for the second cycle and so forth to C14, C15 for the final eighth cycle. Converter 101 of FIGS. 2A and 2B produces an enable signal E responsive to the spreading factor SF to control the activation of the adder component inputs from registers $R_R$ and $R_I$ accordingly.

Figure 5:
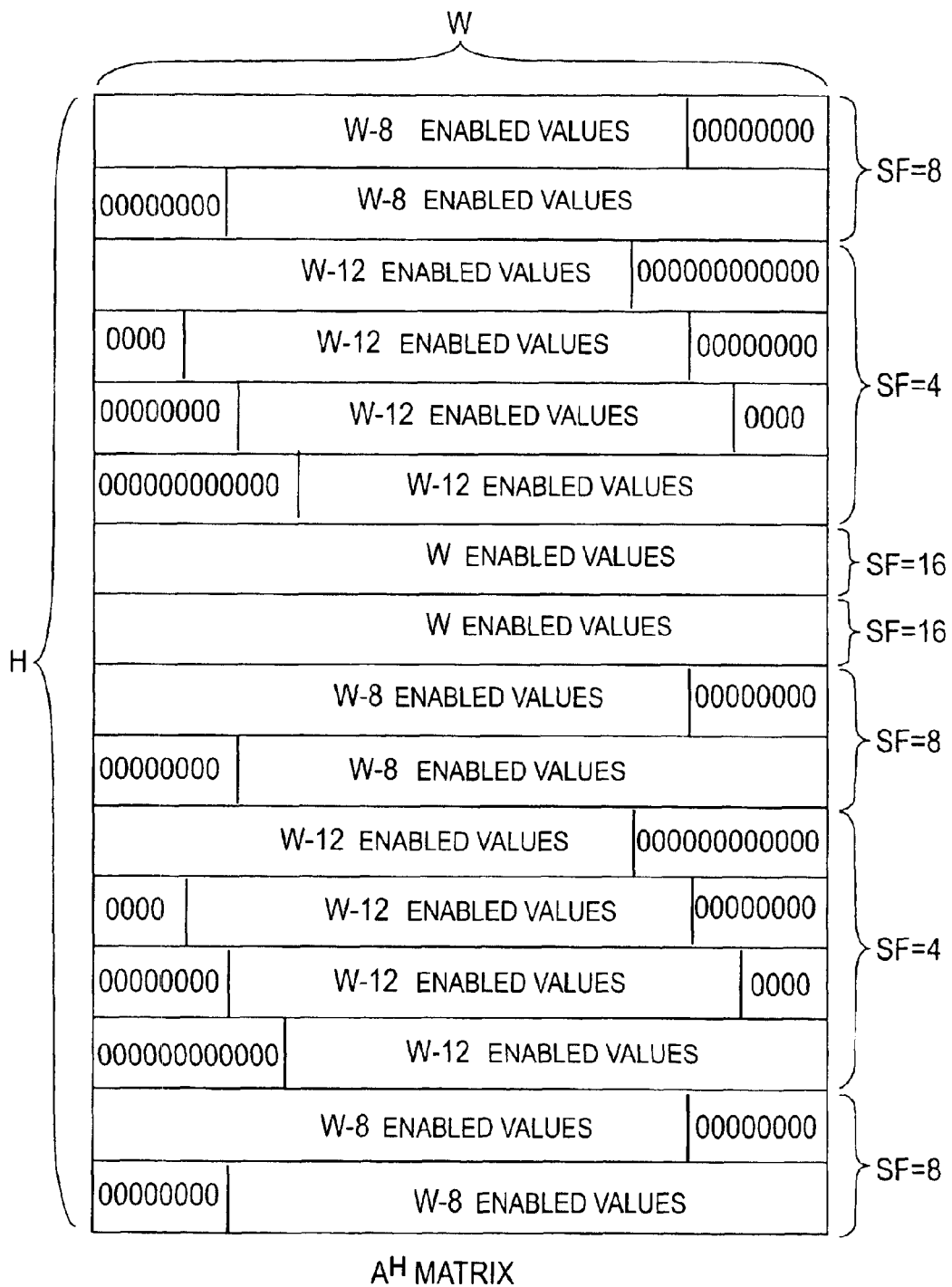
FIG. 5 shows dimensions of a system transmission matrix complex conjugate transpose $A^H$.

FIG. 5 shows a block-tuplet structure of system transmission coefficient matrix $A^H$ with dimensions H×W, where H=16 is based on a preferred maximum number of possible vectors for the communication system. In order to fill the sixteen rows of the matrix, sixteen operational cycles on a channel response sequence are performed, each operational cycle controlled by a channel code to determine values of one row of vectors on the $A^H$ matrix. For a series of N values where N=57, each matrix row contains W=72 values such that the series is processed until the last N value passes through the last register location. N, W and H can vary depending on the particular communication system.

In 3GPP, a standard resource unit RU is defined by a spreading factor SF. The spreading factor SF represents the number of chips per bit for a particular RU, or the bit rate. Consequently, an RU with a spreading factor SF=8 has twice the bit rate of an RU with spreading factor SF=16. Thus, as shown in rows 7 and 8 of FIG. 5, one row of the matrix $A^H$ is used for each RU with a spreading factor equal to 16, as only one processing cycle of the channel response value set through registers $R_R$ and $R_I$ is necessary. An RU with a spreading factor equal to 8 requires two processing cycles and, accordingly, occupies two rows of the matrix. For a spreading factor equal to 4, an RU occupies 4 rows of the matrix for four passes of the channel response. Similarly, an RU with a spreading factor equal to 2, fills 8 rows, and an RU with a spreading factor equal to 1, fills all 16 rows. The system is designed such that if 15 rows are filled, the final operation is performed for an RU with spreading factor equal to 16. Otherwise, the last row of the matrix is filled with zeros since any other spreading factor could not fit within one matrix row. Likewise, for all other combinations, as the remaining rows become occupied, the system accommodates accordingly with appropriate spreading factors.

As shown in FIG. 5, for spreading factor 16, the entire row of the matrix is filled with calculated coefficient values of convolution results. For all other spreading factors, a block of consecutive zeros at either or both ends of the matrix row is produced due to the enable signal E controlling the adder tree inputs, which forces selected zero value inputs during the process. For example, with spreading factor SF=8, the last 8 values of row 1 are zeros since only the inputs associated with the first 8 locations of the registers are active and they will contain a zero value during the last 8 cycles of the first operation cycle. Similarly, the first 8 values of row 2 in the matrix (associated with the second processing cycle results) are zeros since the adder tree inputs associated with locations C0 through C7 are inactive and locations C8 through C15 have values of zero during the first 8 process iteratives of the second pass.

FIG. 6 shows the effect of the enable signal E on the adder components for the spreading factor SF=1. During the first pass of the channel response, only input from location C0 will be processed by adder components A5 and A19 since adder tree inputs from locations C1 to C15 will be inactive as controlled by the enable signal E. During the second pass, input from register location C1 provides the sole input to the adder trees, and so on, until the sixteenth cycle, when only register location C15 provides enabled input to the adders.

Although the invention has been described in part by making detailed reference to certain specific embodiments, such detail is intended to be instructive rather than restrictive. It will be appreciated by those skilled in the art that many variations may be made in the structure and mode of operation without departing from the spirit and scope of the invention as disclosed in the teachings herein.

What is claimed is:

1. An apparatus for convolution of channel codes and a plurality of received channel response values of a CDMA communication signal to produce transmission matrix coefficients, comprising:

a real component shift register $R_R$ and an imaginary component shift register $R_I$, each register having a series of $2^N$ locations;

a first real component adder circuit having a series of $2^{N-1}$ selectively controllable inputs, coupled with the register $R_R$ at the $2^N$ locations that are even numbered;

a second real component adder circuit having a series of $2^{N-1}$ selectively controllable inputs, coupled with the register $R_I$ at the $2^N$ locations that are odd numbered;

a first imaginary component adder circuit having a series of $2^{N-1}$ selectively controllable inputs coupled with the register $R_R$ at the $2^N$ locations that are odd numbered;

a second imaginary component adder circuit having a series of $2^{N-1}$ selectively controllable inputs coupled with the register $R_I$ at the $2^N$ locations that are even numbered;

a real component combiner circuit coupled to the first and second real component adder circuits for outputting a combined real component value;

an imaginary component combiner circuit coupled to the first and second imaginary component adder circuits for outputting a combined imaginary component value; and said registers $R_R$, $R_I$ operable to shift the channel response values sequentially by one location at a time, while receiving a new value in the first location to thereafter generate a next set of channel response values.

2. The apparatus of claim 1 wherein each input is controllable via a binary control bit within the channel code, where the control bits collectively correspond to a $2^N$ bit binary value and each control bit associated with a location of register $R_R$ is the same as the control bit associated with corresponding location of register $R_I$, such that the input receives data from the location to which it coupled as a value or an inverse value of the received data, dependent upon the value of the control bit.

3. The apparatus according to claim 1 where the channel response values are a series of X values and the communication signal has a spreading factor of $2^M$ where M is a positive integer $\leq N$, and a series of Y data values represents a row of values of a system transmission coefficient matrix, further comprising:

a control circuit that operatively controls the registers and adder circuits based on the spreading factor of a communication corresponding to the series of X values to be processed;

said control circuit operative to sequentially input the series of X values followed by a series of $2^{N-1}$ zero values to the registers $2^{N-M}$ times to produce $2^{N-M}$ series of the Y data values, where $Y=X+2^N-1$; and said control circuit operative to selectively enable and disable the inputs of the adder circuits when $2^M<2^N$ such that each time the series of X values is input to the registers, a different set of $2^M$ inputs are enabled from each register with all other adder inputs being disabled.

4. An apparatus according to claim 1 wherein each adder circuit comprises a tree of $2^{N-1}-1$ adders.

5. An apparatus according to claim 4 wherein N=4 so that each register has sixteen locations and wherein each adder circuit has eight inputs and a tree of seven adders.

6. An apparatus according to claim 5 wherein the register location data are binary values and each adder circuit input comprises a selectively operable two's complement circuit that receives a value from the register location corresponding with the input and sends the received value to the adder tree if the corresponding control bit is one or the two's complement of the received value if the control bit is zero.

7. An apparatus according to claim 1 wherein:

the real component combiner circuit includes a subtracter for subtracting the value of the output of the first real component adder circuit that is coupled with the real component register $R_R$, from the value of the output of the second real component adder circuit that is coupled with the imaginary component register $R_I$, to produce the combined real component value; and the imaginary component combiner circuit includes:
   an adder for adding the value of the output of the first imaginary component adder circuit that is coupled with the real component register $R_R$, with the value of the output of the second imaginary component adder circuit that is coupled with the imaginary component register $R_I$, to produce a sum value; and a two's complement circuit coupled to the adder to receive the sum value and produce a two's complement thereof as the combined imaginary component value.

\* \* \* \* \*

UNITED STATES PATENT AND TRADEMARK OFFICE
CERTIFICATE OF CORRECTION

PATENT NO. : 6,959,034 B2 Page 1 of 1
DATED : August 17, 2004
INVENTOR(S) : Buchert et al.

It is certified that error appears in the above-identified patent and that said Letters Patent is hereby corrected as shown below:

Column 4,
Line 7, after "component", delete "All" and insert -- A11 --.

Signed and Sealed this

Seventh Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,959,034 B2
DATED : October 25, 2005
INVENTOR(S) : Buchert et al.

It is certified that error appears in the above-identified patent and that said Letters Patent is hereby corrected as shown below:

Column 4,
Line 7, after "component", delete "All" and insert -- A11 --.

This certificate supersedes Certificate of Correction issued March 7, 2006.

Signed and Sealed this

Eleventh Day of April, 2006

JON W. DUDAS
*Director of the United States Patent and Trademark Office*